United States Patent [19]
Harwin

[11] Patent Number: 5,876,455
[45] Date of Patent: Mar. 2, 1999

[54] BIO-SHIM

[76] Inventor: Steven F. Harwin, 1050 Park Ave., New York, N.Y. 10028

[21] Appl. No.: 899,713

[22] Filed: Jul. 24, 1997

[51] Int. Cl.$^6$ .............................. A61F 2/28; A61B 17/56
[52] U.S. Cl. ................................................. 623/16; 606/72
[58] Field of Search ................................. 623/16, 13, 15; 606/60, 72

[56] References Cited

U.S. PATENT DOCUMENTS

| | | | |
|---|---|---|---|
| 5,324,308 | 6/1994 | Pierce | 606/72 |
| 5,632,748 | 5/1997 | Beck, Jr. et al. | 606/72 |
| 5,647,874 | 7/1997 | Hayhurst | 606/72 |

*Primary Examiner*—David J. Isabella
*Attorney, Agent, or Firm*—Graham & James LLP

[57] ABSTRACT

A graft fixation device such as for use in holes drilled into the intercondylar notch of the femur for a bone-patella tendon-bone constructs, for immediate and secure fixation of both ends of a graft. The device comprises a wedge shaped shim constructed of a hard (preferably metal) biologically inert material, which is wedged in between the graft and the formed tunnel in which the graft is positioned. One side of the shim is arcuate and adapted to be from one third to one half a complete circle circumference (adapted to fit into holes of varying circumferences). The shim is either wedge shaped or formed with central aperture for insertion of an expander such as a screw, to snug up and securely wedge an adjacent graft within a bone hole. The shim does not entail bone damage such as occurs with screw fixation devices, and can be adjusted to the correct and secure holding pressure. The shim is also removable and/or replaceable for different sizes as required.

8 Claims, 3 Drawing Sheets

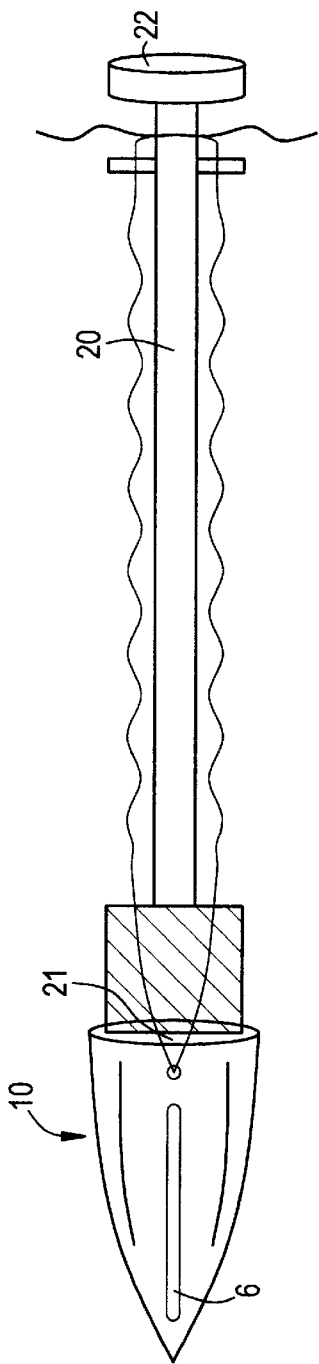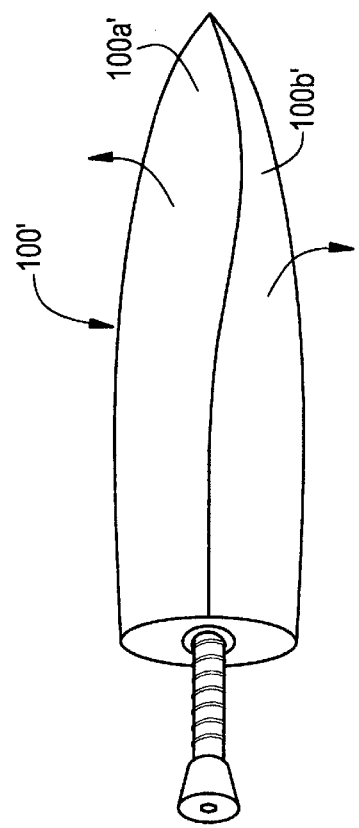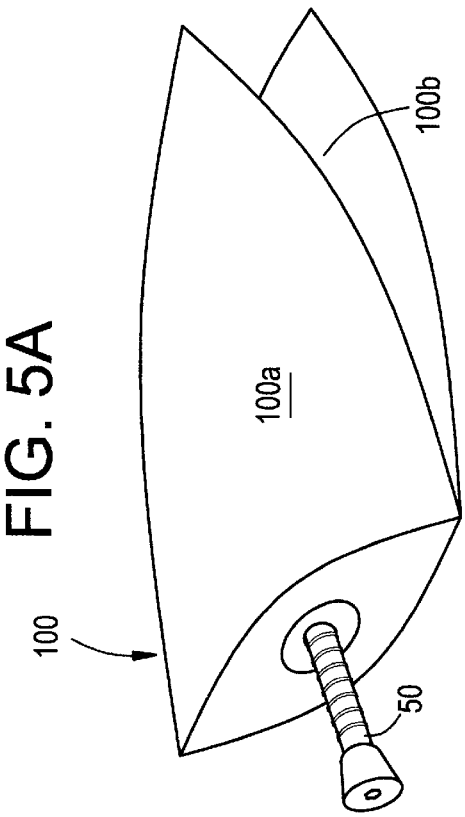

BIO-SHIM

FIELD OF THE INVENTION

This invention relates to devices for fixation of grafts in bones and particularly to grafts in femoral holes in a bone-patella tendon-bone fixation procedure.

BACKGROUND OF THE INVENTION

Reconstruction of the anterior and posterior cruciate ligaments is an increasingly popular orthopedic operation resulting from an increasingly active lifestyle of the populace. Strenuous physical activities involved in this type of lifestyle may cause injuries which result in instability of the knee which must be reconstructed, generally in the form of the aforementioned ligament reconstruction procedures. In addition to correcting knee instability, ligament reconstruction may also provide a secondary beneficial effect of possibly reducing the incidence of secondary arthritis or secondary meniscal tears.

Of the general ligament reconstruction procedures, the most popular is that of "bone-patella tendon-bone". In this procedure or technique, a central 9 or 10 mm portion of the patella tendon is harvested with its attachment onto the patella and tibial tubercle, with a plug of bone which is usually about 25 mm in length and about 9 or 10 mm in width. The graft itself may be cylindrical or trapezoidal in shape depending on surgeon preference.

In the procedure, a hole is drilled into the intercondylar notch of the femur on the lateral side just above the "over-the-top" position. This follows formation of a hole in the tibia which extends from the anteromedial surface into the center of the tibial articular surface, about 7 mm from the posterior cruciate ligament. The bone-patella tendon-bone construct is threaded up through the tibia into the knee and then pulled into the femoral hole. In order for the patient to immediately begin a range of motion program, it is desirable, if not necessary, to provide immediate and secure fixation for both ends of the grafts, whereby the patient can move the knee and begin early bearing exercises.

Several fixation devices have been developed and are available in order to provide the requisite secure fixation. The most popular of such devices is the "interference" screw, with a biologically inert screw being inserted in the femoral hole at the interface between the bone plug of the graft and the host femoral bone. The threads of the screw bite into the graft and the host bone and hold the graft firmly against the bone. The screw can be inserted at the femoral side and the tibial side, but the tibial side is more problematic, particularly if the graft is too short or too long. Accordingly, on the tibial side, the graft is often "posted" via sutures attached to the graft over a cancellous screw and washer, inserted into the tibial bone at some distance away from the previously drilled tibial hole.

There are however, problems and shortcomings which are associated with the "interference" screw fixation procedure. Foremost of these problems is an inherent one related to the operation of the fixation screw. The graft or the posterior cruciate ligament may be damaged by the very insertion of the interference screw, generally as a result of the threads which must bite into the bone for operable fixation. Furthermore, the screw head, because of its close juxtaposition, may impinge on the graft, thereby contributing to further stretching and/or rupture thereof. Size of the screw is also of critical importance since an oversized screw can crush the graft and an undersized screw will provide inadequate fixation. Use of a screw of an incorrect size often will also disrupt the integrity of the fixation site or graft, thereby necessitating use of a different fixation means. This is particularly true on the femoral side and an adjunct technique then becomes necessary. On the tibial side, problems arise with posting such as loosening of the graft and difficulty in tying sutures over the post with adequate tension in order to keep the graft appropriately taut. Often the graft will loosen or the sutures will loosen or the sutures may be cut or severed by the screw threads. If a change is needed, the screw must be removed and another must be reinserted, which can further compromise the graft.

SUMMARY OF THE INVENTION

It is an object of the present invention to provide a method and device for the fixation of bone grafts, particularly grafts in femoral holes in a bone-patella tendon-bone fixation procedure, with reduced graft and bone damage and increased reliability.

It is a further object of the present invention to provide such method and device wherein the device is readily removed or replaced.

It is a still further object of the present invention to provide a method and device for greater control over appropriate fixation of bone grafts and wherein incorrect size is not a critical factor for correction.

Generally the present invention comprises a method of fixation of a graft in a bone and a device for effecting such method. The method and device are of particular applicability with respect to bone-patella tendon-bone constructs, for immediate and secure fixation of both ends of a graft. The method comprises the steps of:

a) inserting a graft into a predrilled hole (tunnel) in a bone;

b) inserting a shim wedge member into a space formed between the graft and the bone hole wall, with the shim wedge member having one side substantially conformed to the bone hole wall configuration for close engaging juxtaposition therewith and another side conformed to the exposed surface of the graft;

c) wedging the shim wedge member into the space to an extent sufficient to fixedly secure the graft against the bone against loosening or removal.

The device comprises the wedge shaped shim (with either an initial wedge form or an in situ formed wedge) constructed of a hard (preferably metal) biologically inert material or bioabsorbable material such as polygalactone, which is wedged in between the graft and the wall of the tunne in which the graft is positioned. One side of the shim is arcuate and adapted to be preferably from one third to one half a complete circle circumference (adapted to fit into holes of varying circumferences). The shim is either tapered (i.e., wedge shaped) and deployed by continued insertion until fixation, by wedging, is sufficient and complete; or the shim is adapted to be expanded once positioned. In this latter embodiment, the shim comprises expander means with an aperture therein, for insertion of an expander element such as a headless screw, into a guideway, causing the shim to be expanded to snug up and securely wedge an adjacent graft within the tunnel.

In either embodiment the shim does not entail bone damage such as occurs with screw fixation devices, and can be adjusted to the correct and secure holding pressure. In the embodiment utilizing an expander screw, the headless screw is removed from close juxtaposition with the graft and does not interfere with the graft. The shim is also advantageously readily removable and/or replaceable for different sizes as required with little or no trauma to the bone or the graft. Another shim may be added for further fixation, if need, without compromise to the graft.

The above objects, features and advantages of the present invention will become more evident from the following discussions and drawings in which:

SHORT DESCRIPTION OF THE DRAWINGS

FIG. 4 depicts an impact tool useful in wedging the shim into fixation position shown in insertion use; and FIGS. 5a and 5b are alternative embodiments of the fixation shim of the present invention which are configured to utilize internally deployed screw expanding elements for effecting wedging fixation.

DETAILED DESCRIPTION OF THE INVENTION

Figure 1A:
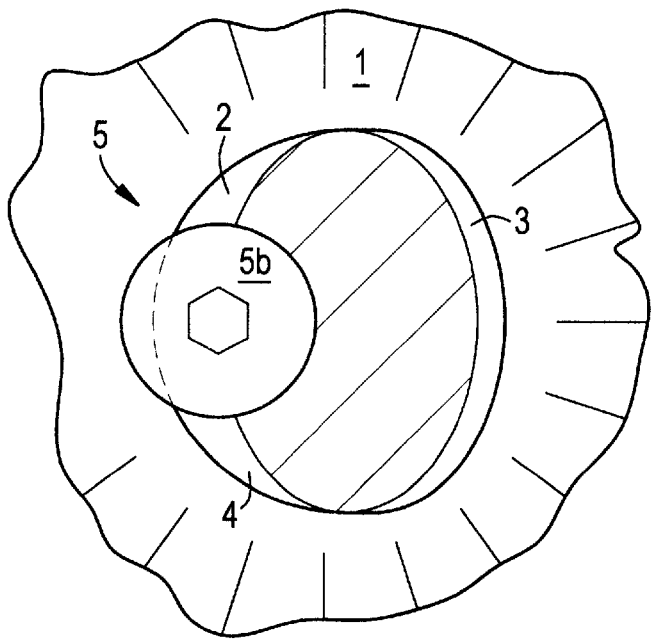
FIGS. 1a and 1b are top and sectioned views respectively of an interference screw of the prior art as used for fixation.

The shim of the present invention is comprised of a biologically inert hard material such as of metals (e.g. such as defined in ASTM 1272 and 1301, for biologically suitable medical implant materials). These include chrome, cobalt, molybdenum, stainless steel alloys (vitalium) with or without porous coating, titanium, and materials other than metal such as sufficiently hard biodegradable materials. Since the shim operates on the basis of a controlled external (relative to the bone and implant) wedging action, there is little danger of graft compromise. There is less or minimal destruction of graft bone tissue on insertion and extraction and the shim is easily extracted if an undersized shim is inadvertently utilized and readily replaced by a larger more appropriate shim without any significant damage. This is in contrast to undersized or oversized fixation screws of the prior art where there is significant damage to the graft with a real and significant fear of loss of fixation or expansion of the tunnel.

For a range of applications it is preferred that the shim be made with various radii sizes for matching with hole sizes in different applications with thickness of the shim ranging from about 6 mm up to about 11 or 12 mm if necessary for revision applications (applications usually too large for effective use of a fixation screw). Generally an appropriate arcuate size of the shim for sufficient holding engagement surface is from about one third to one half of a circle with the remaining circumference of an extrapolated circle being formed by the graft and/or wall of the hole in the bone. Typical hole sizes used for a variety of procedures range from about 7 mm to 10 mm diameters, with the shim having an arc of about ⅓ the circumferences of the hole in which it is used. Length of the shim ranges in 5 mm increments from about 15 to 30 mm, with the larger holes requiring the longer lengths for appropriate fixation.

In order to achieve the requisite wedging action and pressure, the shim may be of a tapered arcuate wedge shape which is forced into position. Alternatively, the shim may be in the form of connected expandable wings with a screw being used to controllably force the wings into the wedge holding configuration. Another configuration is that of an expandable cylinder similar to a wall anchor plug which is expandable with a screw insertion. In these embodiments, the screw is sufficiently removed from the graft whereby it does not interfere therewith.

With the wedge embodiment, forced insertion may be controllably effected by insertion of a clamping device. In order to prevent rotation within the tunnel during insertion, the shim is preferably configured with small stabilizing fins on the surface engaging the bone. The same surface is preferably also provided with a longitudinal cannulation for access to and engagement with an engagement tool as described or with a small compactor akin to a brad setting tool which provides an impact insertion. The exposed end of the shim (when positioned in the bone) is further provided with an extraction hole for the ready removal thereof with minimal trauma when and if necessary. The shim may be inserted over a guide wire or pin previously placed in the space between the graft and the bore hole with the wire or pin guidingly fitted in the cannulation.

The surface of the shim is roughened such as by use of microbeads or a plasma spray is used to reduce incidence of slippage. Alternative, the shim surface itself is roughened or made porous to enhance interfacial contact or coated with an enhancing substance such as hydroxy apatite and the like.

In accordance with the present invention, the graft may be of any shape and configuration with the shim being adpated into conformity therewith for wedging contact.

DETAILED DESCRIPTION OF THE DRAWINGS AND THE PREFERRED EMBODIMENTS

Figure 1B:
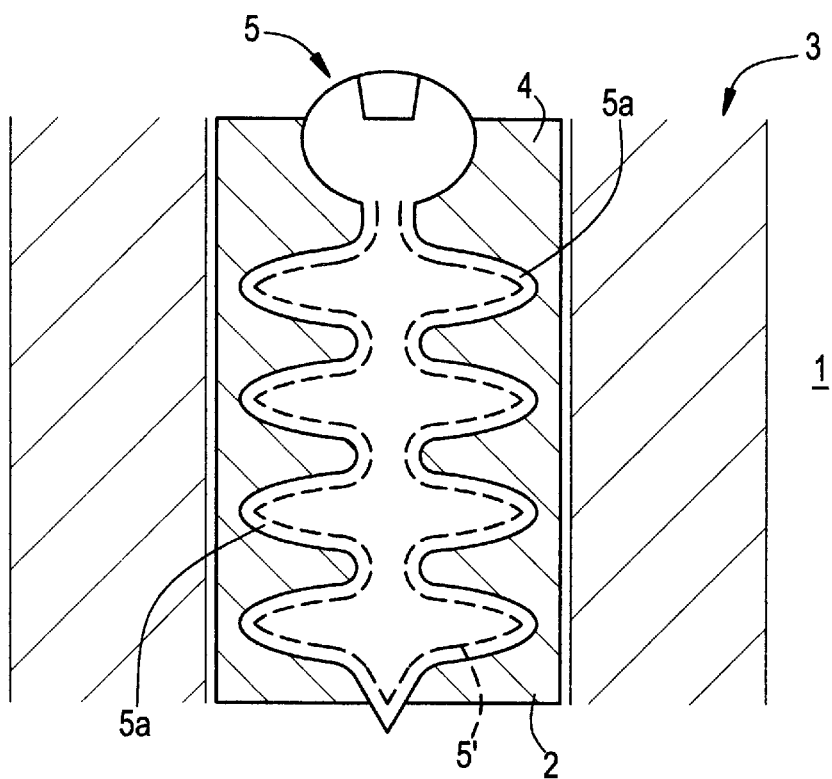

With specific reference to the drawings, In FIGS. 1a and 1b, a bone 1 is drilled to provide hole 2 for insertion of bone graft 3 therein. The bone graft 3 is sized, together with the hole 2, to fit therein with a remaining spacing or tunnel 4 for use in tightening or fixing the bone graft in place. As shown in FIGS. 1a and 1b, the fixation is effect by means of insertion of interference screw 5 which, as shown in FIG. 1b, bites into both the bone and the graft via its threads 5a. In addition, as seen in FIG. 1a, the screw head 5b interferingly impinges on the bone graft.

Figure 2:
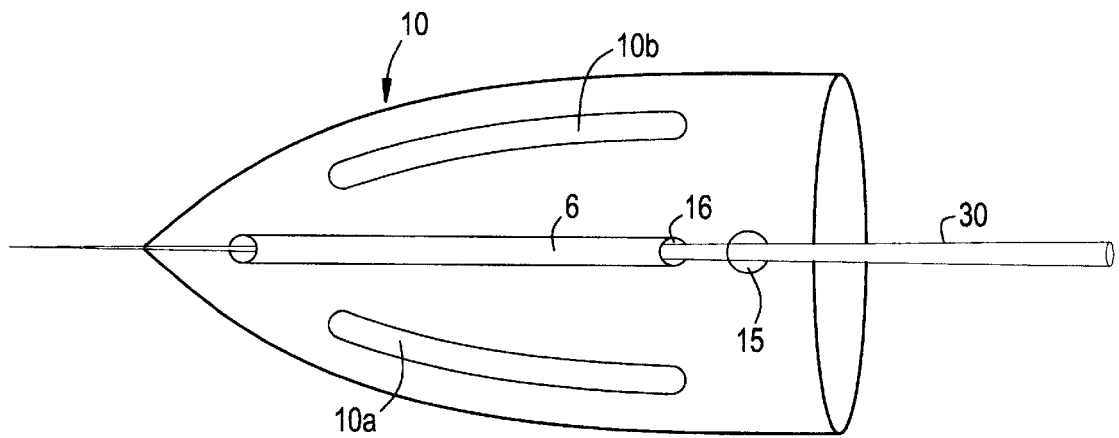
FIG. 2 is an isometric view of the fixation shim of the present invention.
Figure 3:
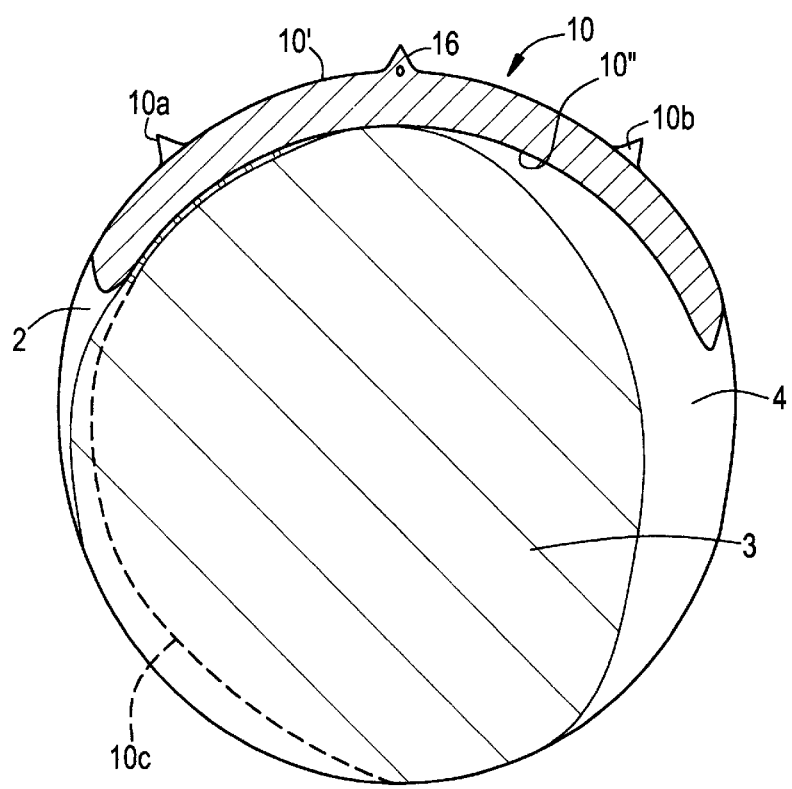
FIG. 3 is a top view showing the fixation shim of FIG. 2 as used in a bone hole to securely fix a graft.

In accordance with the present invention, fixation shim 10, shown in FIG. 2, is closely sized to initially loosely fit within tunnel 4 and is wedge shaped with increasing dimension to tightly fit within the tunnel to effect the requisite fixation as shown in FIG. 3. The shim 10 is arcuate in form to maximize wedging against the adjacent walls of hole 2 and is generally about ⅓ the circumference of the hole 2, with the remaining ⅔ generally comprising the interface between the bone graft and the walls of the hole 2. The shim 10 is selected to be of the appropriate size prior to placement. A too large shim will not be insertable and a too small shim is readily extractable for exchange with a proper size. In contrast, an insufficiently size screw 5' shown in FIG. 1b with effect a partial but insufficient holding at the edge of the threads thereof.

The shim 10 is comprised of two stabilizing fins 10a and 10b on its surface 10' which contacts the bone hole walls, in order to keep it in position and alignment during insertion. This surface is further cannulated with an insertion channel 6 which is used in conjunction with an impactor insertion tool 20, as shown in FIG. 4 and used for guided positioning with guide wire 30 which was previously positioned within hole or tunnel 2. The guide wire 30 is fitted within the cannulation 6 and pin guide hole 16 in the shim 10, for the guided insertion thereof into a proper predetermined position. The insertion end 21 of the tool is sized to fit within channel 6 whereby impact on end 22 forces the shim 10 into wedging position. Hole 15 is used for effecting extraction of the shim should it become necessary or if the shim is of improper size or position, or in case of infection or revision. Alternatively, as seen in phantom FIG. 3, a second shim may be installed 10*c* may be installed at a different part of the circumference in order to fill in any further gaps between the graft and the holes of the wall in order to effect a full pressure shim fitting.

Surfaces 10' and 10", contacting the bone hole walls and graft respectively, are optionally roughened, e.g., with beads or sprayed with a plasma spray or other coating such as hydroxy apatie and the like, to facilitate the interfacial wedging both at the time of insertion and on long term standing.

In the embodiments shown in FIGS. 5*a* and 5*b*, the shims 100 and 100' respectively are configured to be expandable with the insertion of a screw 50. Shim 100 is configured with separating wings 100*a* and 100*b*. Shim 100' is configured with expanding cylindrical sections 100*a'* and 100*b'*. In such embodiments, the shim is simply dropped or pressed into place and then wedging is effected by insertion of the screw to expand the wing or cylinder section. However, the headless screw is completely enclosed from contacting the bone or the graft and the screw is distanced from the graft by a partial thickness of the shim and the screw accordingly does not detrimentally impinge on the graft.

It is understood that the above description and drawings are merely exemplary of the present invention and that changes in the configuration of the shim as well as changes in the applicable base sites for use therewith, are possible without departing from the scope of the present invention as defined in the following claims.

What is claimed is:

1. A method of fixation of a graft in a bone comprising the steps of:
    a) inserting a graft into a predrilled hole in a bone, with a space remaining between the graft and a portion of the wall of the hole;
    b) inserting a one piece shim wedge member into the space formed between the graft and the bone hole wall, with the shim wedge member having one side substantially conformed to the bone hole wall configuration, adjacent thereto, for close engaging juxtaposition therewith and another side of the shim wedge member being conformed to at least a portion of an adjacent exposed surface of the graft;
    c) wedging the shim wedge member into the space to an extent sufficient to solely thereby fixedly secure the graft against the bone and prevent loosening.

2. The method of claim 1, wherein the hole is in the femur for insertion of a graft in a bone-patella tendon-bone fixation.

3. The one piece shim wedge member as used in the method of claim 1, wherein said shim wedge member comprises a wedge shaped shim constructed of a hard biologically inert material, adapted to be fixedly wedged in a space between a graft, positioned in a hole in a bone, and walls of the hole.

4. The one piece shim wedge member of claim 3, wherein a first side of the shim is arcuate and is adapted to have an arc length of from about one third to one half the circumference of a circle defined by the arcuate section, and wherein the shim comprises a second side adapted to be wedgingly adjacently juxtaposed against the graft.

5. The one piece shim wedge member of claim 4, wherein the first side comprises stabilizing means for prevention of rotational movement of the shim during insertion thereof into the hole.

6. The one piece shim wedge member of claim 4, wherein the first side comprises a cannulation adapted to receive an insertion tool therein, whereby impact forces exerted on the tool transmit the forces to the shim wedge member for forced insertion of the shim into the space.

7. The one piece shim wedge member of claim 6, wherein the shim comprises an extraction hole formed therein, which extraction hole is accessible external to the shim for engagement with a tool for the removal of the shim from the hole.

8. The one piece shim wedge member of claim 6 wherein said cannulation is adapted to be guidingly engaged with a guide wire pre-inserted in said space and wherein the shim wedge member comprises an eyelet hole member adjacent an end of the cannulation for insertion therein of the guide wire for guided insertion of the shim wedge member into the hole along said guide wire.

* * * * *